United States Patent [19]

Ishida

[11] Patent Number: 5,403,304
[45] Date of Patent: Apr. 4, 1995

[54] BLOOD COLLECTION DEVICE

[75] Inventor: Noboru Ishida, Fujinomiya, Japan

[73] Assignee: Terumo Kabushiki Kaisha, Tokyo, Japan

[21] Appl. No.: 161,205

[22] Filed: Dec. 2, 1993

Related U.S. Application Data

[63] Continuation of Ser. No. 693,342, Apr. 30, 1991, abandoned.

[30] Foreign Application Priority Data

May 2, 1990 [JP]  Japan .................................. 2-116183

[51] Int. Cl.6 ................................................ A61J 1/00
[52] U.S. Cl. ..................................... 604/403; 604/408; 604/409
[58] Field of Search ................... 604/4, 5, 6, 405, 406, 604/408, 409, 410

[56] References Cited

U.S. PATENT DOCUMENTS

| | | | |
|---|---|---|---|
| 4,025,618 | 5/1977 | Garber et al. | |
| 4,609,372 | 9/1986 | Carmen et al. | 604/410 |
| 4,623,343 | 11/1986 | Thompson | 604/405 |
| 4,804,363 | 2/1989 | Valeri | 604/6 |
| 4,846,795 | 7/1989 | Minagawa | 604/410 |
| 4,938,758 | 7/1990 | Al-Sioufi | |
| 4,943,287 | 7/1990 | Carmen | 604/4 |
| 5,026,347 | 6/1991 | Patel | 604/410 |
| 5,089,146 | 2/1992 | Carmen et al. | 604/406 |
| 5,098,371 | 3/1992 | Juji et al. | 604/4 |

FOREIGN PATENT DOCUMENTS

| | | |
|---|---|---|
| 0116726 | 8/1984 | European Pat. Off. |
| 0084512 | 7/1983 | France |
| 2539010 | 4/1976 | Germany |
| WO83/01573 | 5/1983 | WIPO |
| WO87/06119 | 10/1987 | WIPO |

*Primary Examiner*—Sam Rimell
*Attorney, Agent, or Firm*—Frishauf, Holtz, Goodman & Woodward

[57] ABSTRACT

A blood collection device having a blood-collecting tube, a needle, a blood container connected to the needle by the blood-collecting tube. The blood container has a blood-storing space containing anticoagulant solution. Two blood-component containers and an erythrocyte-preserving solution container are connected to the blood container by a blood-component supplying tube and a tube. The containers are made of soft material. A branching member is coupled to the blood-collecting tube and located between the blood container and the needle. A tube branching from the blood-collecting tube is connected to a filter. The filter allows passage of gas but substantially prevents passage of blood, bacteria, microorganism and the like. A flow stopper connects the blood-collecting tube to the filter. The flow stopper comprises a breakable member closing the branch tube. When the breakable member is broken, the branch tube communicates with the filter.

18 Claims, 8 Drawing Sheets

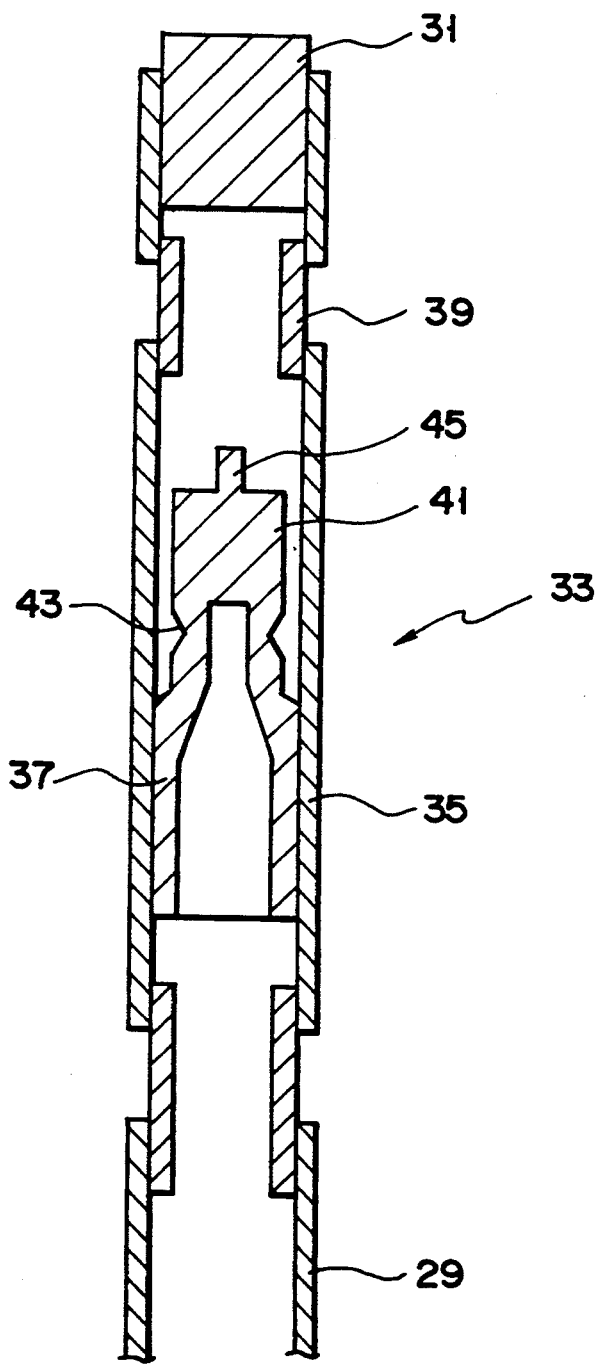
F I G. 2

BLOOD COLLECTION DEVICE

This application is a continuation of application Ser. No. 07/693,342, filed Apr. 30, 1991, now abandoned.

BACKGROUND OF THE INVENTION

1. Field of the Invention

The present invention relates to a blood collection device and, more particularly, to a blood collection device which can not only easily collect blood but also preserve the collected blood fresh for a long period of time, without damaging the blood which is to be analyzed.

2. Description of the Related Art

In recent years, blood-containers made of soft synthetic resin such as soft vinyl chloride resin have come into common use. The use of these containers has rendered component transfusion more common, wherein the blood collected from a donor are divided under aseptic condition into various components such as dense erythrocytes, plasma, platelets, and an anti-hemophilic factor. Component transfusion is applied in order to transfuse to the patient only those components which the patients needs to have, thereby lessening the physical burden on him or her, or thereby to reduce the possibility of immunity-related side effects.

Before applying transfusion to the patient, so-called "cross matching test" is performed in order to determine whether or not the donor's blood matches the patient. This is because, firstly, it is needed to confirm the donor's ABO blood type is the same as that of the patient. Further, even if the donor's blood and the patient's are of the same ABO type, it has to be checked whether aggregation or hemolysis will occur or not due to irregular antibodies contained in the donor's blood or the patient's.

One of the methods of performing cross matching test is to use a blood-collecting tube connected to a needle, as a pilot tube for determining the type of the donor's blood. This method will be described in detail.

In the method, a blood collection device 60 such as the one shown in FIG. 8 is used to collect blood from a donor, and also to separate the blood into components. As is illustrated in FIG. 8, the device 60 comprises a needle 61, a blood-collecting tube 63, a main blood-collecting bag 65, a connecting tube 67, two auxiliary blood-collecting bags 69, 73, and two branching tube 71 and 75, and an erythrocyte-storing bag 77. The needle 61 is attached to one end of the blood-collecting tube 63. The other end of the tube 63 is connected to the main blood-collecting bag 65. The main blood-collecting bag 65 is connected to the second auxiliary blood-collecting bag 69 by means of the connecting tube 67. The tube 67 is connected to the first blood-collecting bag 73 by the branching tube 71, and also to the erythrocyte-storing bag 77 by the branching tube 75.

The erythrocyte-storing bag 77 is filled with normal saline or the like, which has been developed for preserving erythrocytes for a long time and which contains glucose, adenin, and colloid osmoregulator (mannitol).

To collect blood by means of this blood collection device, the needle 61 is inserted into the donor's blood vessel. The blood is collected into the main bag 65 through the needle 61 and the blood-collecting tube 63. The main bag 65 is filled with an anticoagulant solution, known as ACD-A solution or CPD solution, and a medical solution for preserving blood. The blood thus collected is mixed with the medical solutions.

Then, the blood-collecting tube 63 which is connected to the needle 61 is knotted tightly, and is cut from the needle 61. The opening end of the tube 63 is sealed. To prevent the blood remaining in the tube 63 from coagulating, the blood-collecting tube 63 is squeezed and collapsed with a roller pinch or the like, thereby introducing the remaining blood from the tube 63 into the main bag 65. After the collected blood is mixed well with the CPD solution or the like, the roller of the pinch is released, whereby the tube 63 inflates itself due to its elasticity. Then, the mixture of the blood and the medical solutions flows from the main bag 65 into the blood-collecting tube 63.

The blood-solution mixture can be sampled from the main bag 65 in the following another method, so that the collected blood may be analyzed. First, the blood is collected from the donor through the needle 61 and the tube 63 into the main blood-collecting bag 65. Next, the blood is mixed with the anticoagulant solution in the main blood-collecting bag 65. Then, the needle 61 is inserted into the rubber plug of an evacuated blood-sampling tube, whereby the blood is sampled from the tube 63 into the evacuated blood-sampling tube and is subjected to various analyses.

In most cases, the amount of blood sampled into the evacuated blood-sampling tube is much greater than the amount contained in the blood-collecting tube 63, and generally two or more evacuated blood-sampling tubes are used. Every time, a portion of the blood-solution mixture flows into an evacuated blood-sampling tube in the way described above, another equal portion of the blood-solution mixture flows from the main blood-collecting bag 65 into the blood-collecting tube 63. The blood-collecting tube 63 is completely filled with the blood-solution mixture at all times.

The tube 63, always filled up with the blood-solution mixture, is sealed at regular intervals by tube sealers or aluminum rings and cut at the sealed portions. As a result of this, a plurality of pilot tubes, each filled with a portion of the collected blood, generally known as "segmented blood" in the art, which is to be subjected to various analyses.

Identical serial numbers are printed on the blood-collecting tube 63, and at least that end portion of the tube 63 which is connected to the main blood-collecting bag 65 remains, not separated from the main bag 65, it is understood who's blood the pilot tubes contain, in accordance with the serial number printed on the tube 63 connected to the main blood-collecting bag 65.

The main blood-collecting bag 65, now filled with the blood-solution mixture, is put into a centrifugal separator. The separator is driven, until one component of the blood is separated from the remaining components. The main bag 65 is removed from the centrifugal separator, and an upper layer component, thus separated from the others in the main bag 65, is supplied into the first auxiliary blood-collecting bag 73 through the connecting tube 67 and the branching tube 71. Then, the main bag 65 is put into the separator again, and the separator is driven until one of the remaining blood components is separated from the others. The main bag 65 is removed from the separator, and an upper layer component, thus separated from the remaining blood components, is supplied into the second blood-collecting bag 69 through the connecting tube 67.

The dense erythrocytes finally remain in the main blood-collecting bag 65. The erythrocyte-preserving solution contained in the bag 77 is transferred into the main bag 65 through the connecting tube 67 and is mixed with the erythrocyte. In the bag 65, the erythrocytes can thus be preserved for a long period of time.

The blood collection device described above is, however, disadvantageous. When the blood-collecting tube 63 is squeezed and collapsed in preparation for pilot tubes each containing segmented blood, the erythrocytes in the blood are destroyed, causing cythemolysis, which adversely affects the erythrocytes.

In the blood-collecting bag 65, the dense erythrocytes are mixed with the normal saline developed for preserving erythrocytes for a long time and containing glucose, adenin, and colloid osmoregulator (mannitol). Hence, the dense erythrocytes can be preserved for about six weeks.

On the other hand, the erythrocytes in the segmented blood contained in each pilot tube, which is mixed with the ACD-A solution or the CPD solution, can be preserved, but usually for only about three weeks if it is refrigerated. After the three-week period, the segmented blood undergoes cythemolysis, and can no longer be used in cross matching test. Consequently, it impossible to determine, from this segment blood, whether or not the donor's blood matches the patient. To use the segmented blood even after the three-week period, pilot tubes can be made in the following method.

The blood-collecting tube 63 is not sealed and cut right after the blood mixed with the CPD solution and the like has been supplied from the main bag 65 into the tube 63. Rather, erythrocyte-preserving solution is introduced into the main bag 65 and mixed with the erythrocytes therein, and then the blood is made to flow from the tube 63 into the main bag 65 by squeezing and collapsing the tube 63 with a roller pinch. Next, the roller of the pinch is released, making the tube 63 inflate due to its elasticity, and hence allowing the blood-solution mixture to flow from the main bag 65 into the blood-collecting tube 63. Finally, the tube 63, now filled up with the blood-solution mixture, is sealed at regular intervals and cut at the sealed portions, thereby forming pilot tubes, each filled with segmented blood.

In this method, the blood-collecting tube 63 are squeezed twice, inevitably increasing the possibility of cythemolysis and adversely influencing the erythrocytes.

When the blood-collecting tube 63 is squeezed with a roller pinch or the like, the blood contained in the tube 63 and mixed with the CPD solution or the like is replaced by the blood contained in the main bag 65 and mixed with the erythrocyte-preserving solution. The replacement cannot always be performed with high accuracy.

SUMMARY OF THE INVENTION

One object of the present invention is to provide a blood collection device, in which a blood-collecting tube need not be squeezed or collapsed with a roller pinch or the like in order to use this tube as a pilot tube, thus preventing destruction or damaging of erythrocytes and, hence, causing no cythemolysis.

Another object of the invention is to provide a blood collection device which mixes the segmented blood with an erythrocyte-preserving solution in a pilot tube, thus preventing cythemolysis in the pilot tube, making it possible to subject the segmented blood to cross matching test immediately before component transfusion is carried out.

According to a first aspect of this invention, there is provided a blood collection device which comprises: blood-collecting means; a blood-collecting tube; a blood container made of soft material, connected to the blood-collecting means by the blood-collecting tube, and defining a blood-storing space; a branching member connected to the blood-collecting tube and located between the blood-collecting means and the blood container; branch tube means connected at one end to the blood-collecting tube by the branching member; a filter connected to the other end of the branch tube means, for passing gas and preventing passage of blood; a flow stopper means located in the branch tube means and positioned between the filter and the blood-collecting tube, for selectively opening the branch tube means.

According to a second aspect of the present invention, there is provided a blood collection device which comprises blood-collecting means; a blood-collecting tube; a blood container made of soft material, connected to the blood-collecting means by the blood-collecting tube, and defining a blood-storing space; a blood-sampling tube connected at one end to the blood container and communicating with the blood-storing space; a filter located in the other end of the blood-sampling tube; and a flow stopper means located in the blood-sampling tube and positioned between the filter and the blood-storing space, for selectively opening the branch tube.

In either device according to the invention, an anticoagulant solution is preferably contained in the blood-storing space. Further, either device can comprise two blood-supplying tubes, an erythrocyte-solution container and a blood-component container connected to the blood container by tubes.

In a preferred embodiment of the invention, the flow stopper means comprises a breakable member which closes the branch tube means or the blood-sampling tube. The breakable member has a hollow portion having a through hole, a solid portion closing the through hole of the hollow portion, and a frangible seal portion connecting the hollow portion and the solid portion. The hollow portion, the solid portion, and the frangible seal portion are integrally formed of hard synthetic resin. The branch tube means or the blood-sampling tube contains means for preventing the solid portion of the breakable member from contacting the filter after it has been disconnected from the hollow portion.

In operation, blood from a donor is collected into the blood container through the blood-collecting means and the blood-collecting tube at first. Next, the flow stopper means is operated, thus connecting the filter to the blood-collecting tube. The blood-collecting tube thereby communicates with the atmosphere. As a result, the blood flows through the blood-collecting tube and drops from the tube into the blood container by virtue of gravity. In the container, the blood is mixed with the anticoagulant solution already contained in the blood container.

Then, all the blood in the blood container is divided into various components including erythrocytes. All components, but the erythrocytes, are transferred into blood-component containers. Then, the erythrocyte-preserving solution is transferred from the the erythrocyte-preserving solution container to the blood container, and is mixed with the erythrocytes in the blood container.

Then, the blood container is squeezed lightly, thus supplying the erythrocytes, now thoroughly mixed with the erythrocyte-preserving solution, into the blood-collecting tube (in the case of the device according to the first aspect of the invention) or into the blood-sampling tube (in the case of the device according to the second aspect of the invention). Since the filter allows passage of gas, though not allowing passage of blood, it releases the air remaining in the blood-collecting tube or the blood-sampling tube into the atmosphere. Therefore, the tube is filled with only the mixture of erythrocytes and the erythrocyte-preserving solution.

Next, the tube is cut into pieces, and each piece of the tube is sealed, by means of a four-point sealer or the like. A required number of pilot tubes are thereby formed, each containing segmented blood.

Hence, in either device of the invention, the blood-collecting tube need not be squeezed or collapsed as in the conventional device in order to introduce the collected blood into the blood container. Hence, there is no possibility that the erythrocytes are destroyed or damaged to cause cythemolysis.

Moreover, since the anticoagulant solution is contained in the blood-storing space, and the container containing the erythrocyte-preserving solution can communicate with the blood container through a tube, the erythrocytes separated from the collected blood can be preserved longer than is possible in the conventional blood collection device. In addition, since the segmented blood sealed in each pilot tube is mixed with medical solution, e.g., the erythrocyte-preserving solution, it can be preserved longer than that sealed in the pilot tube prepared by the conventional blood collection device. Further, the segmented blood, in which no cythemolysis takes places, can be subjected to cross matching test immediately before the component transfusion of the identical blood filled in the blood container.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is an enlarged, cross-sectional view showing the filter and flow stopper of the device shown in FIG. 1;

DETAILED DESCRIPTION OF THE PREFERRED EMBODIMENTS

A few embodiment of the present invention will now be descried, with reference to the accompanying drawings.

Figure 1:
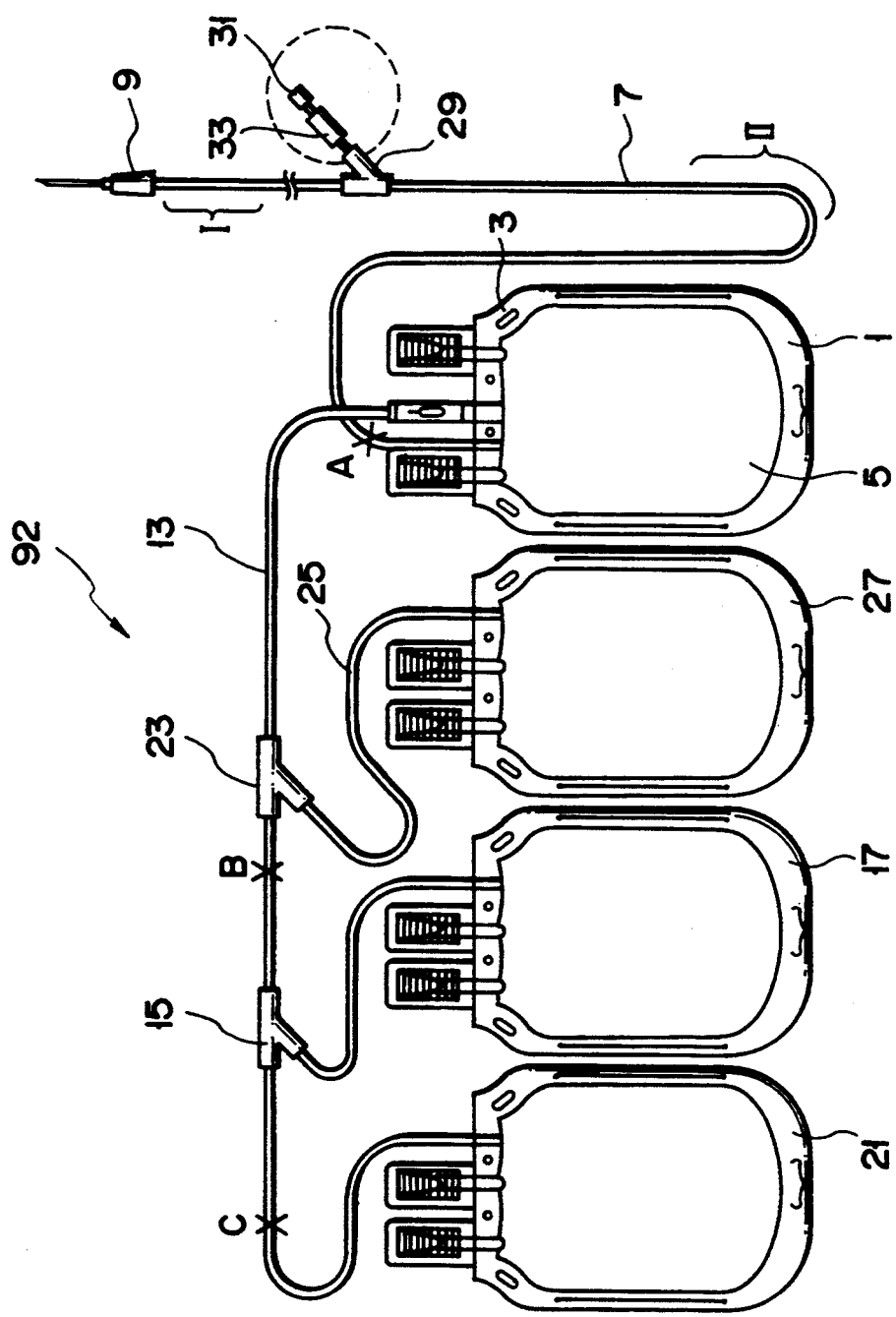
FIG. 1 is a diagram illustrating a blood collection device according to a first embodiment of the present invention.

FIG. 1 shows a blood collection device 92 according to the first embodiment of the invention. As is shown in this figure, this device comprises a blood-collecting bag 1 (hereinafter called "main bag") for storing blood collected from a donor. The main bag 1 is made of soft synthetic resin such as vinyl chloride. Its peripheral edge 3 is heat-sealed by means of high-frequency heating. The main bag 1 has a blood-storing space 5. A blood-collecting tube 7, which is made of soft synthetic resin, too, is connected at one end to the upper end of the main bag 1.

The blood-storing space 5 is filled with an anticoagulant solution such as ACD-A solution (containing 2.20% of sodium citrate, 0.80% of citric acid, and 2.20% of grape sugar), CPD solution (containing 2.63% of sodium citrate, 0.327% of citric acid, 2.32% of grape sugar, and 0.251% of monosodium, phosphate, CPDA solution (containing 2.63% of sodium citrate, 0.327% of citric acid, 2.90% of grape sugar, 0.251% of monosodium phosphate, and 0.0275% of adenin). A needle 9 is attached to the other end of the blood-collecting tube 7.

A blood-component container 17 (hereinafter referred to as "first auxiliary bag") is connected to the main bag 1 by a blood-component supplying tube 13 and a branching member 15. Another blood-component container 21 (hereinafter referred to as "second auxiliary bag") is connected to the main bag 1 by the blood-component supplying tube 13 and the branching member 15. Further, an erythrocyte-preserving solution container 27 is connected to the main bag 1 by the blood-component supplying tube 13, a branching member 23 and an erythrocyte-preserving solution supplying tube 25.

Instead of the two auxiliary bags 17 and 21, only a single auxiliary bag (not shown) can be connected to the main bag 1, or three or more auxiliary bags can be connected to the main bag 1, in accordance with the number of blood components which should be collected independently of one another, The tube 25 for supplying the erythrocyte-preserving solution can be directly coupled to the main bag 1, not by the branching tube 23 nor the blood-component supplying tube 13. Similarly, the first and second auxiliary bags 17 and 21 can be connected to the main bag 1 by two blood-collecting tubes, respectively only, using no branching tubes at all. A connector can be used to alernaitively connect each of the tubes for the respective auxiliary bags 17 and 21 to the main bag 1 rather than using the type of tube directly connecting each of the auxiliary bags to the main bag.

The erythrocyte-preserving solution container 27 is filled with an erythrocyte-preserving solution. The erythrocyte-preserving solution includes normal saline containing glucose, adenin, and colloid osmoregulator (mannitol); a solution containing ascorbic acid-2-sodium phosphate, a monosaccharide (e.g., glucose) and/or an oligosaccharide (e.g., maltose); and a solution containing a monophosphate derivative of a monosaccharide.

A branching member 29 is mounted on the middle portion of the blood-collecting tube 7. This member 29 has an open end. A flow stopper 33 is coupled at one end to the open end of the branching member 29, and at the other end to a filter 31. The filter 31 allows passage of gas, but does not substantially allow passage of blood, bacteria, microorganism and the like. The flow stopper 33 has a breakable member which prevents communication between the blood-collecting tube 7 and the filter 31. When necessary, the breakable member is broken, thereby to establish communication between the tube 7 and the filter 31.

FIG. 2 is an enlarged, cross-sectional view showing that part of the blood collection device which is encircled by the broken circle in FIG. 1, i.e., the branching member 29, the filter 31, and the flow stopper 33. As is evident from FIG. 2, the flow stopper 33 comprises a tube 35, a hollow portion 37, and a solid portion 41. The tube 35 is made of soft vinyl chloride resin or the like. The hollow portion 37 is made of a hard synthetic resin such as a polycarbonate or a hard vinyl chloride resin. It has an outside diameter substantially equal to the inside diameter of the tube 35 and fitted in the tube 35. The solid portion 41 is made of the same material as the hollow portion 37 and formed integrally therewith. The solid portion 41 has a diameter less than the inside diameter of the tube 35 and greater than the inside diameter of the hollow portion 37.

As is shown in FIG. 2, the junction between the hollow portion 37 and the solid portion 41 is a frangible seal portion 43. The seal portion 43 can easily be broken. When this portion 43 is broken, the solid portion 41 is separated from the hollow portion 37, thus establishing communication between the blood-collecting tube 7 and the filter 31. In other words, unless or until the frangible portion 43 is broken, the flow stopper 33 prevents any fluid from flowing between the tube 7 and the filter 31.

A plate-like projection 45 protrudes from the end of the solid portion 41. The projection 45 has a width nearly equal to the outside diameter of the solid portion 41 and greater than the inside diameter of a tube 39 which connects the tube 35 to the tubular case of the filter 31. (In FIG. 2, only the length of the projection 45 is perceived.) Hence, the projection 45 prevents the solid portion 41 from closing the tube 39 after the solid portion 41 is separated from the hollow portion 35.

The filter 31, which allows passages of gas but substantially not the passage of blood, bacteria, microorgainism and the like as has been described, can be a sintered body made by packing polyethylene powder, polypropylene powder or nylon powder in a mold, and then heating and molding at atomosphere. Alternatively, the filter can be a membrane filter comprised of a polyester resin base and a vinyl chloride coating formed on the resin base. The membrane filter can be substituted by a membrane formed of unwoven polyethylene fabric and a polytetrafluoroethylene layer laminated on the fabric, a membrane formed of an acetate film and a silicone coating formed on the acetate film, or a membrane formed of unwoven glass fiber fabric and a fluoro plastics corted on the fabric.

Among the above filters, the filter formed of the sintered polyethylene powder is preferably used. The average size of the particles of the powder is in the range of 20 to 500 $\mu$m, preferably 150 to 250 $\mu$m. The average diameter of the pores of the filter after sintered is preferably in the rage of 0.2 to 50 $\mu$m. More preferably the average diameter of the pores is 10 to 20 $\mu$m so that the filter prevents the passage of blood, bacteria, microorganism and the like, as well as having an appropriate poromeric characteristics. The filter has preferably the thickness of 2 to 3 mm, more preferably 1.5 to 2.5 mm, so as to prevent the passage of blood and so forth, and have a proper gas permeability.

The water tightness of the filter is preferably in the range of 0.15 to 0.3 $kgf/cm^2$, more preferably 0.2 $kgf/cm^2$. If the water tightness is higher than 0.3 $kgf/cm^2$, the gas permeability is degraded. The water tightness is measured under the condition in which a static hydraulic pressure is put on the filter from one side thereof for five seconds at room temperature, and decided from the maximum value when water is not leaked.

The gas permeability is preferably less than 2.0 seconds when it is decided from a necessary time for air of 100 ml to pass the filter at room temperature, measured by B type Gurley Densometer.

When polyethylene is used as a material of the filter, polyethylene powder (average particle size of 200 $\mu$m) is packed in a mold and heated for 5 to 20 minutes (preferably 10 minutes) at 120° to 200° C. (preferably 140° to 160° C.) so that a filter having the average pore diameter of 10 to 15 $\mu$m, the water tightness of about 0.2 $kgf/cm^2$, the gas permeability of 2.0 seconds and the thickness of 2.5 mm is obtained.

It will now be explained how to use the blood collection device, with reference to FIGS. 1 and 2.

First, blood is collected from a donor into the main bag 1 through the needle 9 and the tube 7.

Then, that portion of the tube 7 which is coupled to the needle 9 is knotted tightly and hence sealed. The blood-collecting tube 7 is cut at the portion between the knot and the needle 9. The open end portion of the tube 7 is separated from the rest of the tube 7.

Next, the frangible portion 43 of the flow stopper 33 is broken, thus separating the solid portion 41 from the hollow portion 37. As a result of this, the blood-tube 7 communicates with the filter 31. The air therefore flows into the tube 7 through the filter 31, and the blood remaining in the tube 7 drops into the main bag 1 by virtue of gravity.

Thereafter, the blood-collecting tube 7 is clamped at point A (FIG. 1). In the main bag 1, the blood collected from the donor is mixed well with the anticoagulant solution, e.g., the CPD solution.

Next, the main bag 1 is placed in a centrifugal separator (not shown). The separator is driven until the blood is divided into an upper layer of plasma-platelet mixture, and a lower layer of erythrocytes. The main bag 1 is removed from the separator. The lower portion of the main bag 1 is squeezed, thereby transferring the plasma-platelet mixture from the bag 1 into the first auxiliary bag 17 through the blood-component supplying tube 13 and the branching member 15. After the plasma has been supplied into the first auxiliary bag 17, the tube 13 is sealed at point B (FIG. 1) and cut at this point 5, whereby the bag 17 and the second auxiliary bag 21 are disconnected from the main bag 1 and the erythrocyte-preserving solution container 27.

The first auxiliary bag 17 is placed in the centrifugal separator. The separator is driven at about 3500 rpm until the platelets precipitate on the bottom of the bag 17. The bag 17 is removed from the separator, and the plasma upper layer is transferred into the second auxiliary bag 21 via the blood-component supplying tube 13. The tube 13 is sealed at point C (FIG. 1) and cut at this point, whereby the second auxiliary bag 21 is disconnected from the first auxiliary bag 17. The plasma contained in the bag 21 can be used in component transfusion, whenever necessary there after.

In the meantime, the erythrocyte-preserving solution is supplied from the erythrocyte-preserving solution container 27 into the main bag 1 through the erythrocyte-preserving solution supplying tube 25 and the blood-component supplying tube 13. This solution is mixed thoroughly with the erythrocytes in the main bag 1.

After the solution and the erythrocytes have been mixed well together, the clamp which clamps the tube 7 at point A is released. Then, the main bag 1 is lightly squeezed to deliver the solution-erythroucyte mixture into the tube 7. As a result of this, the air remaining in the tube 7, the branching member 29, and the flow stopper 33 flows into the atmosphere through the filter 31. Nevertheless, the filter does not allow passage of the solution-erythrocyte mixture into the atmosphere. The blood-collecting tube 7 is filled with the solution-erthrocyte mixture only.

The blood-collecting tube 7, now filled with the mixture of the erythrocytes and the erythrocyte-preserving solution, is cut and sealed by means of a four-point sealer. A required number of pilot tubes are thereby formed, each containing segmented blood.

Since the segmented blood in each pilot tube is the mixture of the erythrocytes and the erythrocyte-preserving solution, the erythrocytes can remain fresh, without undergoing hemolysis, for about six weeks if the segmented blood is cooled at appropriate temperatures. Hence, the segment blood can be used in cross matching test, immediately before the erythrocytes in the main bag 1 is transfused to a patient, provided that the test is carried out within six weeks from the forming of the pilot tubes.

Figure 3:
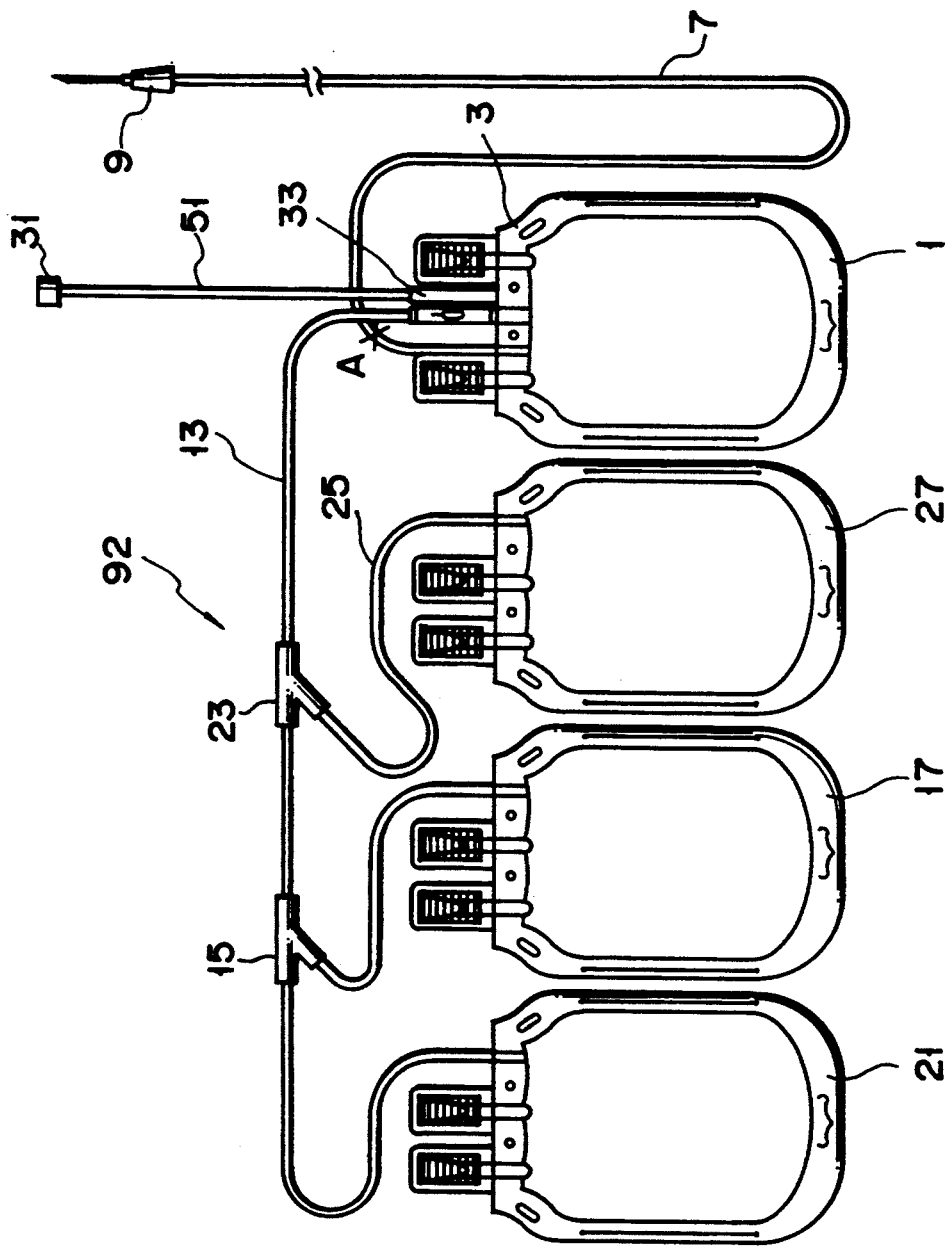
FIG. 3 is a diagram showing a blood collection device according to a second embodiment of the present invention.

With reference to FIG. 3, a blood collection device according to the second embodiment of the invention will be described. The second embodiment is different from the first embodiment (FIG. 1), in three respects only. First, a blood-sampling tube 51 is connected at one end to a main bag 1. Second, a flow stopper 33 is provided at the junction between the main bag 1 and the tube 51. Third, a filter 31 is connected to the other end of the blood-sampling tube 51.

It will now be explained how to use the blood collection device shown in FIG. 3.

First, blood is collected from a donor into the main bag 1 through the needle 9 and a blood-collecting tube 7. Then, the tube 7 is sealed and cut at point A. The blood in the main bag 1 is divided into plasma, platelets, and erythrocytes, exactly in the same way as in the case of the first embodiment (FIG. 1). Next, the erythrocyte-preserving solution is supplied from a erythrocyte-preserving solution container 27 into the main bag 1 and mixed with the erythrocytes in the main bag 1, also in the same way as in the first embodiment (FIG. 1).

Thereafter, the frangible portion 43 of the flow stopper 33 is broken, thus separating the solid portion 41 from the hollow portion 37. As a result of this, the blood-storing space of the main bag 1 communicates with the filter 31. Then, the main bag 1 is squeezed, expelling the air from the tube 7, the branching member 29 and the flow stopper 33 into the atmosphere through the filter 31, and allowing the solution-erythrocyte mixture to flow into the blood-sampling tube 51.

Next, the blood-sampling tube 7, filled with the erythrocytes-solution mixture, is cut and sealed by means of a four-point sealer. A required number of pilot tubes are thereby formed, each containing segmented blood.

Figure 4:
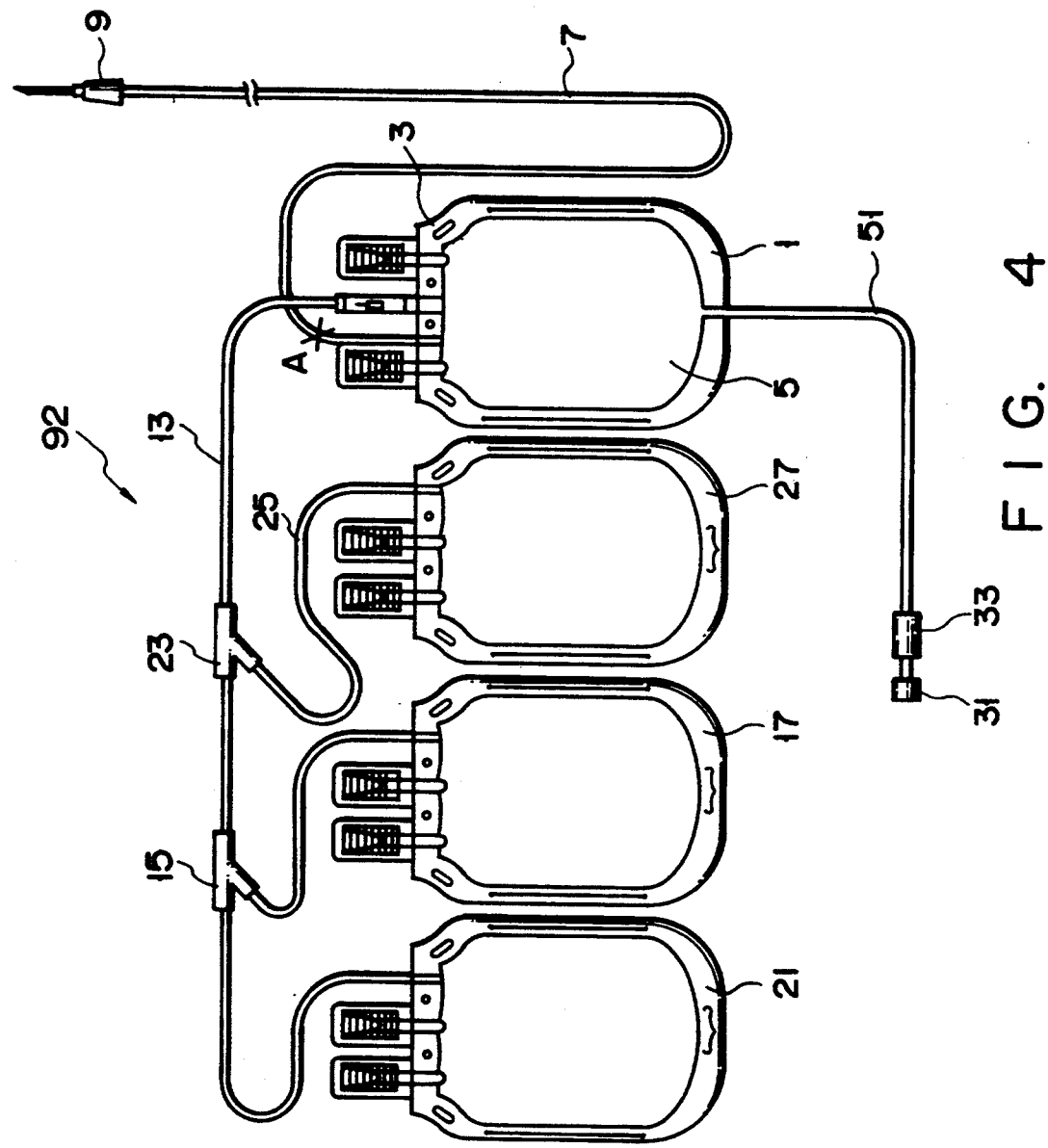
FIG. 4 is a diagram illustrating a blood collection device according to a third embodiment of the present invention.

With reference to FIG. 4, a blood collection device according to the third embodiment of the invention will be described. The third embodiment is identical to the second embodiment (FIG. 3), except for one respect only. More specifically, a blood-sampling tube 51 is connected to the lower portion of a main bag 1. Obviously, the erythrocytes, which are precipitated on the bottom of the main bag 1, can be introduced into the tube 51 more easily than in the case of the second embodiment (FIG. 3) wherein the blood-sampling tube 51 is connected to the top of the main bag 1.

Figure 5:
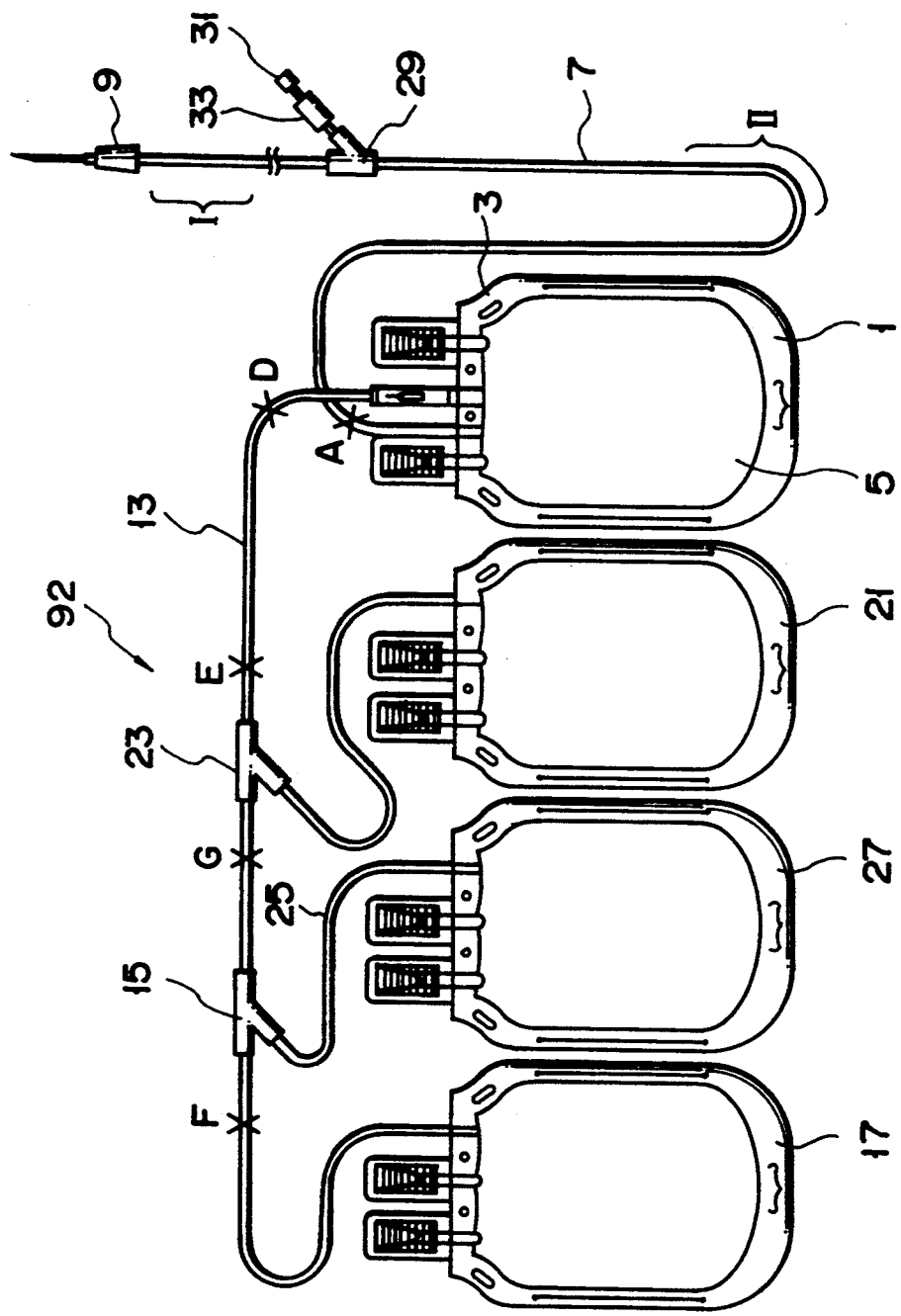
FIG. 5 is a diagram representing a blood collection device according to a fourth embodiment of the present invention.

With reference to FIG. 5, a blood collection device according to the fourth embodiment of the invention will be described. The fourth embodiment is identical to the first embodiment (FIG. 1), except for three respects. First, a first auxiliary bag 17 is connected to a main bag 1 by a blood-component supplying tube 13 and a branching member 15. Second, an erythrocyte-preserving solution container 27 is coupled to the main bag 1 by the tube 13, the branching member 15, and an erythrocyte-preserving solution supplying tube 25. Third, a second auxiliary bag 21 is connected to the main bag 1 by the tube 13 and a branching member 23.

It will be explained how to use the blood collection device illustrated in FIG. 5.

First, about 400 ml of blood is collected from a donor into the main bag 1 through a needle 9 and a blood-collecting tube 7. Then, that end portion I of the tube 7 which is connected to the needle 9 is knotted tightly and hence sealed. The blood-collecting tube 7 is cut at the portion between the knot and the needle 9. The open end of the tube 7 is separated from the rest of the tube 7.

Next, the frangible 43 portion of a flow stopper 33 connected to the tube 7 is broken, thus separating the hollow portion 37 and the solid portion 41. As a result, the blood-collecting tube 7 communicates with a filter 31 coupled to the flow stopper 33. The blood remaining in the portion II of the tube 7 is thereby made to drop into the main bag 1 by virtue of gravity.

Further, the blood-collecting tube 7 is clamped at point A (FIG. 5). In the main bag 1, the blood collected from the donor is mixed well with the anticoagulant solution, e.g., the CPD solution.

The main bag 1 is placed in the centrifugal separator. The separator is driven at about 3500 rpm until the blood is divided into an upper layer of plasma, an intermediate layer, or a buffy coat (i.e., a layer of platelet-leukocyte mixture), and a lower layer of erythrocytes.

The lower portion of the main bag 1 is squeezed, thereby transferring the plasma into the first auxiliary bag 17 through the blood-component supplying tube 13 and the branching member 15. The lower portion of the main bag 1 is further squeezed, thereby transferring the mixture of the plasma-rich platelets and the leukocytes, in an amount of about 32 g, into the second auxiliary bag 21 via the blood-component supplying tube 13 and the branching member 23. Then, about 51 g of plasma is transferred from the first auxiliary bag 17 into the second auxiliary bag 21. As a result, the second auxiliary bag 21 contains about 83 g of blood components.

Thereafter, the erythrocyte-preserving solution is supplied from the container 27 into the main bag 1 via the tube 25, the branching member 15 and the tube 13. The solution is mixed well with the erythrocytes in the main bag 1.

After the solution is mixed thoroughly with the erythrocytes, the blood-component supplying tube 13 is clamped by a clamp at point D (FIG. 5) near the main bag 1. The main bag 1 is then lightly squeezed, thereby supplying the solution-erythrocyte mixture into the blood-collecting tube 7. As a result of this, the air remaining in the tube 7, the branching member 29, and the flow stopper 33 is expelled into the atmosphere through the filter 31. Nevertheless, the filter 31 does not allow passage of the solution-erythrocyte mixture into the atmosphere. A portion II of the blood-collecting tube 7 is, therefore, filled with the solution-erythrocyte mixture only.

The blood-collecting tube 7, now filled with the erythrocytes mixed with the erythrocyte-preserving solution, is cut and sealed by means of a four-point sealer. A required number of pilot tubes are thereby formed, each containing segmented blood.

Since the segmented blood in each pilot tube is the mixture of the erythrocytes and the erythrocyte-preserving solution, the erythrocytes can remain fresh, without undergoing hemolysis, for about six weeks if the segmented blood is cooled at appropriate temperatures. Hence, the segment blood can be used in cross matching test, immediately before the erythrocytes in the main bag 1 is transfused to a patient, provided that the test is carried out within six weeks from the forming of the pilot tubes.

Then, the blood-component supplying tube 13 is sealed and cut at points E and F (FIG. 5) by means of tube sealers. The second auxiliary bag 21 is placed in a centrifugal separator (not shown). The separator is driven at 800 rpm for 6.5 minutes, whereby the contents of the bag 21 is divided into an upper layer of platelet-rick portion and a lower layer of the mixture of leukocytes and erythrocytes.

Next, 40 g of the plasma-rich platelets is transferred from the second auxiliary bag 21 into the container 27 which is now empty. The platelets contained in the container 27 can be transfused into a patient whenever necessary.

The blood-component supplying tube 13 is sealed and cut at point G, thus disconnecting the second auxiliary bag 21 from the container 27. The residual leukocytes and the residual erythrocytes in the second auxiliary bag 21 are abandoned.

Figure 6:
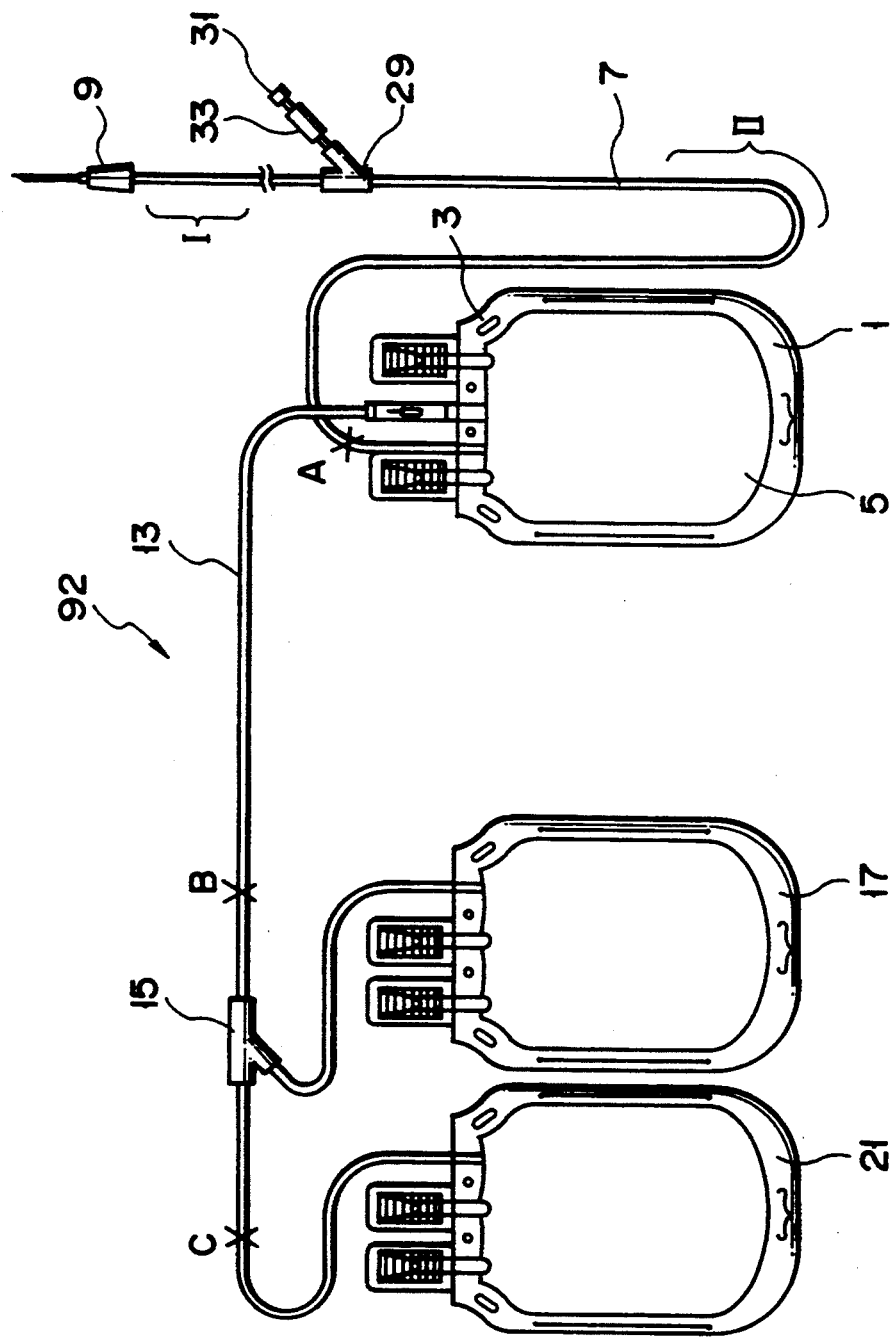
FIG. 6 is a diagram illustrating a blood collection device according to a fifth embodiment of the present invention.

FIG. 6 illustrates a blood collection device according to the fifth embodiment of the invention. This device is different from the device of FIG. 1, only in that it has no containers for an erythrocyte-preserving solution.

It will be explained how the device of FIG. 6 is used to collect blood from a donor and to form pilot tubes.

First, blood is collected from the donor into a main bag 1 through a needle 6 and a blood-collecting tube 7. Then, that end portion I of the tube 7 which is connected to the needle 9 is knotted tightly and hence sealed. The blood-collecting tube 7 is cut at the portion between the knot and the needle 9. The open end of the tube 7 is separated from the rest of the tube 7.

Next, the frangible portion 43 of a flow stopper 33 connected to the tube 7 is broken, thus separating the hollow portion 37 and the solid portion 41. As a result, the blood-collecting tube 7 communicates with a filter 31 coupled to the flow stopper 33. The blood remaining in the portion II of the tube 7 is thereby made to drop into the main bag 1 by virtue of gravity.

Further, the blood-collecting tube 7 is clamped at point A (FIG. 6). In the main bag 1, the blood collected from the donor is mixed well with the anticoagulant solution, e.g., the CPD solution.

The main bag 1 is placed in the centrifugal separator. The separator is driven at about 2000 rpm until the blood is divided into an upper layer of platelet-rich plasma and a lower layer of erythrocytes.

Next, the lower portion of the main bag 1 is squeezed, thereby transferring the plasma-platelet mixture from the main bag 1 into the first auxiliary bag 17 through a blood-component supplying tube 13 and a branching member 15. Then, the tube 13 is sealed and cut at point B (FIG. 6), whereby the bag 17 and a second auxiliary bag 21 are disconnected from the main bag 1.

Further, the first auxiliary bag 17 is placed in a centrifugal separator (not shown). The separator is driven at about 3500 rpm until the platelets precipitate on the bottom of the bag 17.

The upper layer of the contents in the first auxiliary bag 17, i.e., the plasma, is transferred from the bag 17 into the second auxiliary bag 21 through the branching member 15. This done, the blood-component supplying tube 13 is sealed and cut at point C, thus disconnecting the bags 17 and 21 from each other. The plasma contained in the second auxiliary bag 21 will be used in component transfusion.

The clamp on the blood-collecting tube 7, located at point A, is released, and the main bag 1 is lightly squeezed. The mixture of erythrocytes and the anticoagulant solution is thereby supplied into the blood-collecting tube 7. As a result, the air remaining in the tube 7, the branching member 29, and the flow stopper 33 is expelled into the atmosphere through the filter 31. Nevertheless, the filter 31 does not allow passage of the mixture of erythrocytes and the anticoagulant solution into the atmosphere. The blood-collecting tube 7 is, therefore, filled with the erythrocyte-solution mixture only.

The blood-collecting tube 7, now filled with the erythrocytes mixed with the anticoagulant solution, is cut and sealed by means of a four-point sealer. A required number of pilot tubes are thereby formed, each containing segmented blood.

As has been pointed out, the erythrocytes in the segmented blood contained in each pilot tube can be preserved for only about three weeks if it is refrigerated. Nevertheless, since the tube 7 need not be squeezed or collapsed with a roller pinch or the like in order to form pilot tubes, the erythrocytes are neither destroyed nor damaged. As a result of this, the segment blood undergoes no hemolysis.

One of the auxiliary bags 17 and 21 can be dispensed with, in the case where it suffices to divide blood into two components, e.g., plasma and erythrocytes, whereby the blood collection device is modified into a so-called "double-bag device" which has one main bag and one auxiliary bag. Further, both auxiliary bags 17 and 21 can be dispensed with, in the case where it suffices to preserve the blood collected from a donor, whereby the blood collection device is modified into a so-called "single-bag device." In other words, the present invention can applied to such a double-bag device and a single-bag device, wherein there is no need to squeeze or collapse the blood-collecting tube with a roller pinch or the like, thus preventing destruction or damaging of erythrocytes and, hence, causing no hemolysis.

Figure 7:
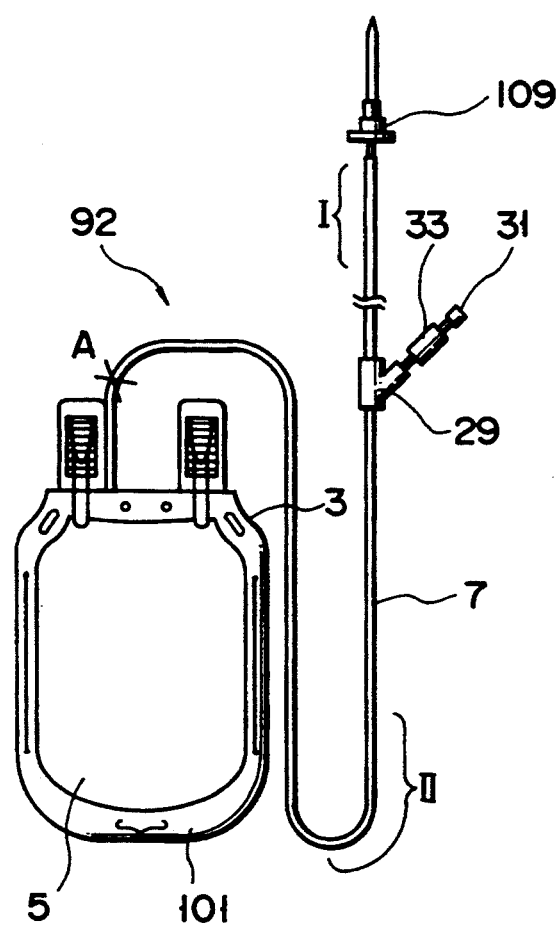
FIG. 7 is a diagram showing a blood collection device according to a sixth embodiment of the present invention.
Figure 8:
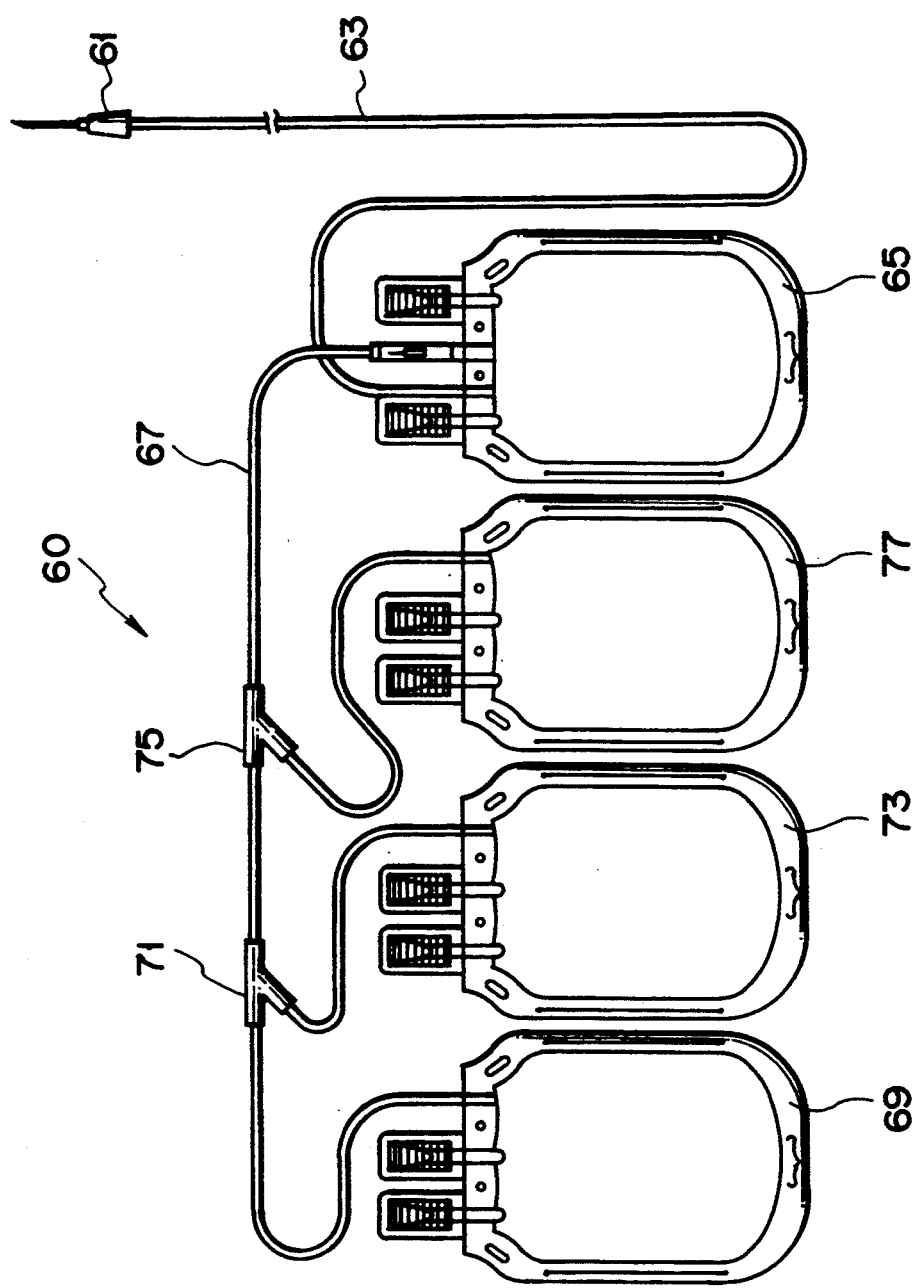
FIG. 8 is a diagram showing a conventional blood collection device.

With reference to FIG. 7, a blood collection device according to a sixth embodiment of the invention will be described. As can be understood from FIG. 7, this device is different from the fifth embodiment (FIG. 6), in three respects. First, an erythrocyte-collecting bag 101 is used in place of the main bag 1. Second, a needle 109 made of plastics and used to be inserted into a bag is provided as blood-collecting means, in place of the needle 9. Third, the device has no auxiliary bags. The erythrocyte-collecting bag 101 contains some amount of erythrocyte-preserving solution. The needle 109 is designed for insertion, not into human blood vessel but into an erythrocyte-containing bag. The bottle needle 109 can be replaced by a connector made of plastics and having a male-tapered hollow cylindrical tip.

It will now be explained how to use the device shown in FIG. 7.

First, a bag (not sown) is prepared which is filled with erythrocytes separated from the other components of blood collected from a donor.

Next, the bottle needle 109 is inserted into the erythrocyte-containing bag, thereby transferring the erythrocytes from this bag into the erythrocyte-collecting bag 101 through a blood-collecting tube 7. Then, that end portion I of the tube 7 which is connected to the needle 109 is knotted tightly and hence sealed. The blood-collecting tube 7 is cut at the portion between the knot and the needle 109. The opened of the tube 7 is separated from the rest of the tube 7.

Next, the frangible 43 portion of a flow stopper 33 connected to the tube 7 is broken, thus separating the hollow portion 37 and the solid portion 41. As a result, the blood-collecting tube 7 communicates with a filter 31 coupled to the flow stopper 33. The blood remaining in the portion II of the tube 7 is thereby made to drop into the main bag 1 by virtue of gravity.

Further, the blood-collecting tube 7 is clamped at point A (FIG. 7). In the main bag 1, the blood collected from the donor is mixed well with the erythrocyte-preserving solution in the erythrocyte-collecting bag 101.

The clamp on the blood-collecting tube 7, located at point A, is released, and the bag 101 is lightly squeezed. The mixture of erythrocytes and the erythrocyte-preserving solution is thereby supplied into the blood-collecting tube 7. As a result, the air remaining in the tube 7 and the flow stopper 33 is expelled into the atmosphere through the filter 31. Nevertheless, the filter 31 does not allow passage of the erythrocyte-solution mixture into the atmosphere. The blood-collecting tube 7 is, therefore, filled with the erythrocyte-solution mixture only.

The blood-collecting tube 7, now filled with the erythrocytes mixed with the anticoagulant solution, is cut and sealed by means of a four-point sealer. A required number of pilot tubes are thereby formed, each containing segmented blood which is the mixture of the erythrocytes and the erythrocyte-preserving solution.

Hence, it is unnecessary to squeeze or collapses the tube 7, with a roller pinch or the like, in order to form pilot tubes, the hrocytes are neither destroyed nor damaged. As a result of this, the segment blood undergoes no hemolysis.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A blood collection device comprising:
   blood-collecting means;
   a blood-collecting tube;
   a blood container formed of a soft material, connected to said blood-collecting means by said blood-collecting tube, said blood container defining a blood-storing space that contains an anticoagulant solution therein;
   a branching member connected to said blood-collecting tube and positioned between said blood-collecting means and said blood container;
   branch tube means having only two end portions, a first end portion connected to said blood-collecting tube via said branching member, said branch tube means further having a second end portion;
   a filter connected to said second end portion of said branch tube means, for passing a gas therethrough and for substantially preventing a passage of an amount of blood therethrough, said filter permitting said gas to pass therethrough in a first direction toward said branch tube means and in a second direction away from said branch tube means; and
   flow stopper means positioned in said branch tube means between said filter and said blood-collecting tube, for selectively opening said branch tube means after a quantity of blood has been collected in said blood storing space, said flow stopper means including a breakable stopper member for opening said branch tube means when said breakable stopper member is broken, wherein breaking of said breakable stopper member opens said branch tube means and permits air to enter said blood-collecting tube via said filter and branch tube means.

2. The device according to claim 1, further comprising means for providing a cross matching test sample by introducing a quantity of dense erythrocytes having an anticoagulant solution added thereto into said blood-collecting tube without cythemolysis of the sample.

3. The device according to claim 2, further comprising an erythrocyte-preserving solution container and at least one tube connecting said erythrocyte-preserving solution container to said blood container.

4. The device according to claim 2, further comprising a blood-component container connected to said blood container by at least one tube.

5. The device according to claim 2, wherein said breakable member comprises:
   a hollow portion positioned in said branch tube means;
   said hollow portion having a through hole formed therein;
   a solid portion closing said through hole of said hollow portion; and a frangible seal portion connecting said hollow portion and said solid portion;

said hollow portion, said solid portion and said frangible portion being formed of a hard synthetic resin; and said hollow portion, said solid portion and said frangible portion being formed integrally with one another.

6. The device according to claim 2, wherein said solid portion includes means for preventing said solid portion from abutting on said filter after said solid portion is separated from said hollow portion by breaking of said frangible portion.

7. The device according to claim 2, further comprising sealing means for sealing a top end portion of said blood-collecting tube after said quantity of blood has been collected in said blood storing space, whereby said flow of gas through said filter in said first and second direction enables a control of a blood flow into and out of said blood-collecting tube without a need to squeeze said blood-collecting tube, thereby preventing a cythemolysis of said blood flowing into and out of said blood collecting tube.

8. A blood collection device comprising:
blood-collecting means;
a blood-collecting tube;
a blood container formed of a soft material, connected to said blood-collecting means by said blood-collecting tube, said blood container defining a blood-storing space that contains an anticoagulant solution therein;
a blood-sampling tube having only two end portions, a first end portion connected to said blood container, said blood-sampling tube being in fluid communication with said blood-storing space, said blood-sampling tube further having a second end portion;
a filter positioned in said second end portion of said blood-sampling tube, for passing a gas therethrough and for substantially preventing a passage of an amount of blood therethrough, said filter permitting said gas to pass therethrough in a first direction toward said blood sampling tube and in a second direction away from said blood-sampling tube; and
flow stopper means positioned in said blood-sampling tube between said filter and said blood-storing space, for selectively opening said blood-sampling tube after a quantity of blood has been collected in said blood storing space, said flow stopper means including a breakable stopper member for opening said blood-sampling tube when said breakable stopper member is broken, wherein breaking of said breakable stopper member opens said blood-sampling tube and permits air to enter said blood-sampling tube via said filter.

9. The device according to claim 8, further comprising means for providing a cross matching test sample by introducing a quantity of dense erythrocytes having an anticoagulant solution added thereto into said blood-sampling tube without cythemolysis of the sample.

10. The device according to claim 9, further comprising an erythrocyte-preserving solution container and at least one tube connecting said erythrocyte-preserving solution container to said blood container.

11. The device according to claim 9, further comprising a blood-component container connected to said blood container by at least one tube.

12. The device according to claim 9, wherein said breakable member comprises:
a hollow portion positioned in said blood-sampling tube, said hollow portion having a through hole formed therein;
a solid portion closing, said through hole of said hollow portion;
a frangible seal portion connecting said hollow portion and said solid portion;
said hollow portion, said solid portion and said frangible portion being formed of a hard synthetic resin; and
said hollow portion, said solid portion and said frangible portion being formed integrally with one another.

13. The device according to claim 12, wherein said solid portion includes means for preventing said solid portion from abutting on said filter after said solid portion has been separated from said hollow portion by breaking of said frangible portion.

14. The device according to claim 9, further comprising sealing means for sealing a top end portion of said blood-sampling tube after said quantity of blood has been collected in said blood storing space, whereby said flow of gas through said filter in said first and second directions enables a control of a blood flow into and out of said blood sampling tube, without a need to squeeze said blood-sampling tube, thereby preventing a cythemolysis of said blood flowing into and out of said blood sampling tube.

15. A blood collection device comprising:
blood-collecting means;
a blood-collecting tube;
a blood container formed of a soft material, connected to said blood-collecting means by said blood-collecting tube, said blood container defining a blood-storing space that contains an anticoagulant solution therein;
a branching member connected to said blood-collecting tube and positioned between said blood-collecting means and said blood container;
branch tube means connected at a first end portion thereof to said blood-collecting tube via said branching member;
a filter connected to a second end portion of said branch tube means, for passing a gas therethrough and for substantially preventing a passage of an amount of blood therethrough, said filter permitting said gas to pass therethrough in a first direction toward said branch tube means and in a second direction away from said branch tube means;
flow stopper means positioned in said branch tube means between said filter and said blood-collecting tube, for selectively opening said branch tube means after a quantity of blood has been collected in said blood storing space;
said flow stopper means including a breakable member for opening said branch tube means when said breakable member is broken;
an erythrocyte-preserving solution container;
at least one tube connecting said erythrocyte-preserving solution container to said blood container; and
a blood-component container connected to said blood container with said at least one tube.

16. A blood collection device comprising:
blood-collecting means;
a blood-collecting tube;

a blood container formed of a soft material, connected to said blood-collecting means by said blood-collecting tube, said blood container defining a blood-storing space that contains an anticoagulant solution therein;

a blood-sampling tube connected, first end portion thereof, to said blood container, said blood-sampling tube being in fluid communication with said blood-storing space;

a filter positioned in a second end portion of said blood-sampling tube, for passing a gas therethrough and for substantially preventing a passage of an amount of blood therethrough, said filter permitting said gas to pass therethrough in a first direction toward said blood-sampling tube and in a second direction away from said blood-sampling tube;

flow stopper means positioned in said blood-sampling tube between said filter and said blood-storing space, for selectively opening said blood-sampling tube after a quantity of blood has been collected in said blood storing space, said flow stopper means including a breakable member for opening said blood-sampling tube when said breakable member is broken;

an erythrocyte-preserving solution container;

at least one tube connecting said erythrocyte-preserving solution container to said blood container; and a blood-component container connected to said blood container by said at least one tube.

17. A blood collection device, comprising:

blood collecting means;

a blood-collecting tube;

a blood container formed of a soft material, connected to said blood-collecting means by said blood-collecting tube, said blood container defining a blood-storing space that contains an anticoagulant solution therein;

a branching member connected to said blood-collecting tube and positioned between said blood-collecting means and said blood container;

branch tube means having only two end portions, a first end portion connected to said blood-collecting tube via said branching member, said branch tube means further having a second end portion;

a filter connected to said second end portion of said branch tube means, for passing a gas therethrough and for substantially preventing a passage of an amount of blood therethrough, said filter permitting said gas to pass therethrough in a first direction toward said branch tube means and in a second direction away from said branch tube means; and flow stopper means positioned in said branch tube means between said filter and said blood-collecting tube, for selectively opening said branch tube means after a quantity of blood has been collected in said blood storing space, said flow stopper means including a breakable stopper member for opening said branch tube means when said breakable stopper member is broken, wherein a cross matching test sample formed of a mixture of blood and said anticoagulant solution is obtained by closing a blood-collecting tube at a portion thereof between said blood-collecting means and branching member after collecting blood into said blood-collecting tube and blood container by said blood-collecting means, and then by breaking said breakable stopper member in said branch tube means and introducing air into said blood-collecting tube through said filter, thereby transferring the blood remaining in said blood-collecting tube into said blood container by virtue of gravity, and then by transferring the blood mixed with said anticoagulant solution in said blood container back to said blood-collecting tube.

18. A blood collection device, comprising:

blood collecting means;

a blood-collecting tube;

a blood container formed of a soft material, connected to said blood-collecting means by said blood-collecting tube, said blood container defining a blood-storing space that contains an anticoagulant solution therein;

a blood-sampling tube having only two end portions, a first end portion connected to said blood container, said blood-sampling tube being in fluid communication with said blood-storing space, said blood-sampling tube further having a second end portion;

a filter positioned in said second end portion of said blood-sampling tube, for passing a gas therethrough and for substantially preventing a passage of an amount of blood therethrough in a first direction toward said blood-sampling tube and in a second direction away from said blood-sampling tube; and flow stopper means positioned in said blood-sampling tube between said filter and said blood-storing space, for selectively opening said blood-sampling tube after a quantity of blood has been collected in said blood storing space, said flow stopper means including a breakable stopper member for opening said blood-sampling tube when said breakable stopper member is broken, wherein a cross matching test sample formed of a mixture of blood and said anticoagulant solution is obtained by closing a blood-collecting tube after collecting blood into said blood-collecting tube and blood container by said blood-collecting means, and then by breaking said breakable stopper member in said sampling-tube and exhausting air in said sampling-tube therefrom, through said filter, thereby transferring the blood mixed with said anticoagulant solution in said blood container to said blood-sampling-tube.

* * * * *

UNITED STATES PATENT AND TRADEMARK OFFICE
CERTIFICATE OF CORRECTION

PATENT NO. : 5,403,304
DATED : April 4, 1995
INVENTOR(S) : ISHIDA

It is certified that error appears in the above-indentified patent and that said Letters Patent is hereby corrected as shown below:

Column 3, line 25, after "it" insert --is--

Column 6, line 16, change "descried" to --described--.

Column 8, line 2, change "corted" to --coated--.

Column 13, line 27, change "sown" to --shown--;
           line 38, change "opened" to --open end--

Column 15, line 9, (claim 6), change "claim 2" to
           --claim 5--

Signed and Sealed this

Twenty-fourth Day of December, 1996

Attest:

BRUCE LEHMAN

Attesting Officer        Commissioner of Patents and Trademarks